United States Patent
Granier et al.

(10) Patent No.: US 7,482,313 B2
(45) Date of Patent: Jan. 27, 2009

(54) BICYCLO(3.3.1)NONANES AND BICYCLO(3.3.1)NONENES AND THEIR USE AS FLAVOR OR FRAGRANCE INGREDIENT

(75) Inventors: Thierry Granier, Duebendorf (CH); Andreas Hanhart, Uster (CH); Jerzy A. Bajgrowicz, Zurich (CH)

(73) Assignee: Givaudan SA, Vernier (CH)

( * ) Notice: Subject to any disclaimer, the term of this patent is extended or adjusted under 35 U.S.C. 154(b) by 365 days.

(21) Appl. No.: 10/597,289

(22) PCT Filed: Jan. 14, 2005

(86) PCT No.: PCT/CH2005/000014

§ 371 (c)(1),
(2), (4) Date: Jul. 19, 2006

(87) PCT Pub. No.: WO2005/070860

PCT Pub. Date: Aug. 4, 2005

(65) Prior Publication Data

US 2008/0274927 A1  Nov. 6, 2008

(30) Foreign Application Priority Data

Jan. 21, 2004 (GB) ................... 0401187.0

(51) Int. Cl.
*C11D 3/50* (2006.01)
(52) U.S. Cl. ............................. 510/104; 512/14; 585/21
(58) Field of Classification Search .................. 510/104; 512/14; 585/21
See application file for complete search history.

(56) References Cited

U.S. PATENT DOCUMENTS

| 4,265,657 A | 5/1981 | Kloek |
| 4,700,008 A | 10/1987 | Takeda et al. |
| 6,008,186 A | 12/1999 | Schulte-Elte et al. |

FOREIGN PATENT DOCUMENTS

| EP | 0 882 697 A | 12/1998 |
| JP | 60 100532 A | 6/1985 |

OTHER PUBLICATIONS

Allen, Charles F. H., Canadian Journal of Chemistry 1967, vol. 45, issue 11, pp. 1201-1207. No month available. Abstract only.*
Search Report from The Patent Office in Great Britain dated May 20, 2004 for application GB0401187.0.
International Search Report dated May 17, 2005 for application PCT/CH2005/000014.
Written Opinion for the International Searching Authority for application PCT/CH2005/000014.
Database WPI, Section Ch, Week 198528, Derwent Publications Ltd., London, GB; AN 1985-169441; XP002328313 -& JP 60 100532 A (Mitsubishi Petrochemical Co Ltd), Jun. 4, 1985 abstract.
Patent Abstracts of Japan, vol. 017, No. 436 (C-1096), Aug. 12, 1993 & JP 05 097755 A (Kao Corp), Apr. 20, 1993 abstract.
Patent Abstracts of Japan, vol. 006, No. 073 (C-101), May 8, 1982 & JP 57 009779 A (Nippon Petrochem Co Ltd), Jan. 19, 1982 abstract.
English-language abstract for EP0882697 obtained online from esp@cenet.

* cited by examiner

*Primary Examiner*—John R Hardee
(74) *Attorney, Agent, or Firm*—Norris McLaughlin & Marcus, PA

(57) ABSTRACT

The present invention relates to substituted bicyclo[3.3.1] nonanes and bicyclo[3.3.1]nonenes of formula (I)

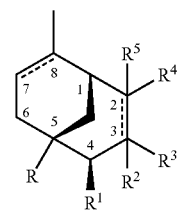

wherein R, and $R^1$ to $R^5$ have the same meaning as described in the specification.

11 Claims, No Drawings

BICYCLO(3.3.1)NONANES AND BICYCLO(3.3.1)NONENES AND THEIR USE AS FLAVOR OR FRAGRANCE INGREDIENT

This is an application filed under 35 USC 371 of 35 USC 371 of PCT/CH2005/000014.

The present invention relates to substitued bicyclo[3.3.1]nonanes and bicyclo[3.3.1]nonenes, having ambery, woody odour notes. This invention relates furthermore to a method of their production and to flavour and fragrance compositions comprising them.

In the fragrance industry there is always an ongoing demand for new compounds that enhance or improve on odour notes, or impart new odour notes.

Surprisingly, we have found a novel class of compounds having much sought-after ambery woody odour notes and which may be produced from readily-available cheap and naturally available starting materials.

In a first aspect the invention refers to a compound of formula (I)

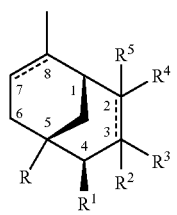

(I)

wherein
- R is isopropyl or iso-propenyl;
- $R^1$ is hydrogen, methyl or ethyl;
- $R^2$ and $R^3$ are independently hydrogen, methyl, or ethyl; or
- $R^2$ and $R^3$ taken together is ethylidene; or
- $R^2$ and $R^3$ taken together is a divalent radical $(CH_2)_2$ which forms cyclopropane together with the carbon atom to which they are attached;
- $R^4$ and $R^5$ are independently hydrogen, hydroxy, $C_1$ to $C_3$ alkoxy, e.g. methoxy, ethoxy, or $C_2$ to $C_3$ acyloxy, e.g. acetoxy; or
- $R^4$ and $R^5$ together with the carbon atom to which they are attached form a 1,3-dioxolane ring or a 1,3-dioxane ring; or
- $R^4$ and $R^5$ together with the carbon atom to which they are attached form a carbonyl group;
- the bond between C2 and C3 is a single bond, or the dotted line together with the bond between C2 and C3 represents a double bond; and
- the bond between C7 and C8 is a single bond, or the dotted line together with the bond between C7 and C8 represents a double bond.

The compounds according to the present invention contain several chiral centres and as such may exist as a mixture of stereoisomers, or they may be resolved as isomerically pure forms. Resolving stereoisomers adds to the complexity of manufacture and purification of these compounds and so it is preferred to use the compounds as mixtures of their stereoisomers simply for economic reasons. However, if it is desired to prepare individual stereoisomers, this may be achieved according to methodology known in the art, e.g. preparative HPLC and GC or by stereoselective syntheses.

Particular preferred compounds of formula (I) are 5-isopropenyl-4,8-dimethylbicyclo[3.3.1]non-7-en-2-one; 4-ethyl-5-isopropenyl-8-methylbicyclo[3.3.1]non-7-en-2-one; 5-isopropenyl-3,4,8-trimethylbicyclo[3.3.1]non-7-en-2-one; 5-isopropenyl-3,3,4,8-tetramethylbicyclo[3.3.1]non-7-en-2-one; 5-isopropenyl-8,8-dimethoxy-2,6-dimethylbicyclo[3.3.1]non-2-ene; 4,8-dimethyl-5-isopropenylspiro[bicyclo[3.3.1]nonane-2,2'-[1,3]dioxolane]; 5-isopropenyl-4,8-dimethylbicyclo[3.3.1]non-7-en-2-ol; 5-isopropenyl-2,4,8-trimethylbicyclo[3.3.1]non-7-en-2-ol; 5-isopropyl-4,8-dimethylbicyclo[3.3.1]nonan-2-one, 5-isopropenyl-8-methylbicyclo[3.3.1]non-7-en-2-one, 5-isopropenyl-3,4,8-trimethylbicyclo[3.3.1]non-7-en-2-one, and 4,8-dimethyl-5-isopropenyl-8-methoxy-bicyclo[3.3.1]non-7-ene.

The compounds according to the present invention may be used alone or in combination with a base material. As used herein, the "base material" includes all known odourant molecules selected from the extensive range of natural and synthetic molecules currently available, such as essential oils, alcohols, aldehydes and ketones, ethers and acetals, esters and lactones, macrocycles and heterocycles, and/or in admixture with one or more ingredients or excipients conventionally used in conjunction with odourants in fragrance compositions, for example, carrier materials, and other auxiliary agents commonly used in the art.

The following list comprises examples of known odourant molecules, which may be combined with the compounds of the present invention:
- ethereal oils and extracts, e.g. tree moss absolute, basil oil, castoreum, costus root oil, myrtle oil, oak moss absolute, geranium oil, jasmin absolute, patchouli oil, rose oil, sandalwood oil, wormwood oil, lavender oil or ylang-ylang oil;
- alkohols, e.g. citronellol, Ebanol™, eugenol, farnesol, geraniol, Super Muguet™, linalool, phenylethyl alcohol, Sandalore™, terpineol or Timberol™.
- aldehydes and ketones, e.g. α-amylcinnamaldehyd, Georgywood™, hydroxycitronellal, Iso E Super®, Isoraldeine®, Hedione®, maltol, methyl cedryl ketone, methylionone or vanillin;
- ether and acetals, e.g. Ambrox™, geranyl methyl ether, rose oxide or Spirambrene™.
- esters and lactones, e.g. benzyl acetate, cedryl actetate, γ-decalactone, Helvetolide®, γ-undecalactone or vetivenyl acetate.
- macrocycles, e.g. ambrettolide, ethylene brassylate or Exaltolide®.
- heterocycles, e.g. isobutylchinoline.

The compounds of the present invention may be used in a broad range of fragrance applications, e.g. in any field of fine and functional perfumery, such as perfumes, household products, laundry products, body care products and cosmetics. The compounds can be employed in widely varying amounts, depending upon the specific application and on the nature and quantity of other odourant ingredients. The proportion is typically from 0.001 to 20 weight percent of the application. In one embodiment, compounds of the present invention may be employed in a fabric softener in an amount of from 0.001 to 0.05 weight percent. In another embodiment, compounds of the present invention may be used in fine perfumery in amounts of from 0.1 to 20 weight percent, more preferably between 0.1 and 5 weight percent. However, these values are given only by way of example, since the experienced perfumer may also achieve effects or may create novel accords with lower or higher concentrations.

The compounds of the present invention may be employed into the fragrance application simply by directly mixing the fragrance composition with the fragrance application, or they may, in an earlier step be entrapped with an entrapment material, for example, polymers, capsules, microcapsules and nanocapsules, liposomes, film formers, absorbents such as carbon or zeolites, cyclic oligosaccharides and mixtures thereof, or they may be chemically bonded to substrates, which are adapted to release the fragrance molecule upon application of an external stimulus such as light, enzyme, or the like, and then mixed with the application.

Thus, the invention additionally provides a method of manufacturing a fragrance application, comprising the incorporation of a compound of formula (I) as a fragrance ingredient, either by directly admixing the compound of formula (I) to the application or by admixing a fragrance composition comprising a compound of formula (I), which may then be mixed to a fragrance application, using conventional techniques and methods.

As used herein, "fragrance application" means any product, such as fine perfumery, e.g. perfume and Eau de Toilette; household products, e.g. detergents for dishwasher, surface cleaner; laundry products, e.g. softener, bleach, detergent; body care products, e.g. shampoo, shower gel; and cosmetics, e.g. deodorant, vanishing creme, comprising an odourant. This list of products is given by way of illustration and is not to be regarded as being in any way limiting.

Compounds of formula (I) wherein $R^4$ and $R^5$ together with the carbon atom to which they are attached form a carbonyl group (see formula (II) below) may be prepared by the reaction of α-pinene with α,β-unsaturated carboxylic acids or derivatives thereof such as alkenoyl halogenide, e.g. crotonyl chloride, crotonyl bromide and pentenoyl chloride; or alkenoyl anhydride, for example crotonic anhydride, in the presence of a catalytic amount of an acid, such as Lewis acid or Bronsted acid.

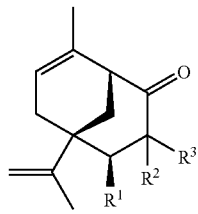

(II)

Surprisingly we have found that certain compounds of formula (I) may also be prepared by reacting α-pinene with β,γ-unsaturated carboxylic acids or β-hydroxy carboxylic acids, resulting in a ketone of formula (II) in the presence of a catalytic amount of an acid. It is believed that, due to the acidic conditions, both the β,γ-unsaturated carboxylic acids and the β-hydroxy carboxylic acids will transfer to the corresponding α,β-unsaturated carboxylic acids, which then will react with α-pinene.

The resulting compounds of formula (II) may be alkylated to give further compounds of formula (I). Still further compounds of formula (I) may be prepared by reduction and/or acylation of the carbonyl group at C2 or by Grignard reaction and acylation of the carbonyl group at C2. Still further compounds of formula (I) may be prepared by hydrogenation.

Compounds of formula (I) wherein either $R^2$ or $R^3$ is not hydrogen, and $R^4$ and $R^5$ together with the carbon atom to which they are attached form a carbonyl group may also be prepared by the reaction of α-pinene with α,β-unsaturated α-alkyl carboxylic acids, e.g. 2-methylcrotonyl chloride, 2-ethylcrotonyl chloride, 2-methylcrotonic anhydride, in the presence of a catalytic amount of an acid.

Optionally pure compounds of formula (I) and enantiomer mixtures of a compound of formula (I) enriched in one enantiomer may be synthesized by starting from the optically pure α-pinene or from an enantiomer mixture enriched in either (S)-(+)-α-pinene or (R)-(–)-α-pinene respectively.

The invention is now further described with reference to the following non-limiting examples.

EXAMPLE 1

5-Isopropenyl-4,8-dimethylbicyclo[3.3.1]non-7-en-2-one (1)

a) A mixture of 30 g α-pinene ((1S)-(–)/(1R)-(+) 90:10, 0.22 mol), 67.8 g crotonic anhydride (0.44 mol, 2 eq.) and 4.95 g zinc bromide (0.021 mol, 0.1 eq.) was heated at 95° C. for 7 h. The reaction mixture was then treated with 50 ml $H_2O$ and heated 3 h at reflux. Extraction with $Et_2O$, drying of the org. phases with $Na_2SO_4$ followed by Vigreux-distillation and FC (Flash Chromatography) ($SiO_2$, hexane/$Et_2O$ 95:5) gave 990 mg (2%) of compound 1. The boiling point of the end product is 80° C. at 0.07 torr (0.09 mbar).

$[α]_D^{22}$=–280.5 (c=0.93, EtOH)

Odour description: woody, resinous, fir, fruity raspberry ketone-like, olibanum-like, ciste, ambery b) According to the procedure described above starting from (–)-α-pinene in the presence of crotonyl chloride at 90° C. for 4 hours.

$[α]_D^{22}$=–785 (c=0.75, EtOH)

Odour description: fruity, woody, piny, ambery c) According to the procedure describe above starting from (+)-α-pinene in the presence of crotonic anhydride at 95° C. for 6 h.

$[α]_D^{22}$=+536.2 (c=1.02, EtOH)

Odour description: grapefruit, red fruit, piny, ambery $^1$H-NMR (400 MHz, $CDCl_3$): δ5.63-5.59 (br. m, H—C(7)), 4.75-4.72 (br. s, $H_t$—CH=), 4.64-4.62 (br. s, $H_c$—CH=), 3.08 (dd, J=6.7, 14.5, $H_α$—C(3)), 2.82-2.78 (br. s, H—C(1)), 2.45-2.31 (m, C(6)$H_2$), 2.27 (quintet t, J=2.0, 7.0, H—C(4)), 2.18 (dd, J=3.3, 12.8, irrad. at 2.80→d, J=12.8, $H_{syn}$—C(9)), 1.89 (dt, J=1.6, 14.5, irrad. at 2.80→dd, J=1.6, 14.0, $H_β$—C(3)), 1.87 (dt, J=2.6, 12.8, irrad. at 2.80→dd, J=2.2, 13.0, $H_{anti}$—C(9)), 1.73 (s, MeC=$CH_2$), 1.66 (br. s, J=1.9, MeC(8)), 0.80 (d, J=7.2, MeC(4)).

$^{13}$C-NMR (100 MHz, $CDCl_3$): δ212.42 (s, CO), 150.75 (s, C(5)C=), 134.36 (s, C(8)), 124.85 (d, C(7)), 108.75 (t, $CH_2$=), 53.98 (d, C(1)), 40.92 (t, C(3)), 39.40 (d, C(4)), 39.25 (t, C(6)), 39.17 (s, C(5)), 31.20 (t, C(9)), 21.79 (q, MeC(8)), 18.42 (q, MeC=$CH_2$), 16.59 (q, MeC(4)).

MS (EI): 204 (34), 189 (8), 171 (4), 161 (11), 147 (19), 134 (30), 133 (50), 119 (99), 105 (78), 97 (93), 93 (100), 91 (87), 77 (49), 69 (28), 41 (70).

IR: $ν_{max}$ 2954, 2877, 1718, 1659, 1445, 1376, 1311, 1292, 1267, 1181, 1101, 1027, 968, 838, 688 $cm^{-1}$.

EXAMPLE 2

4-Ethyl-5-isopropenyl-8-methylbicyclo[3.3.1]non-7-en-2-one (2)

At 30° C., a mixture of 7.35 g of 2-pentenoyl chloride (62 mmol) and 1.7 g of zinc chloride (12 mmol, 0.2 eq.) in 85 ml ethylene chloride was treated dropwise within 20 min. with a solution of 19.4 g of (–)-alpha-pinene (142 mmol, 2 eq.) in 20 ml ethylene dichloride. The reaction mixture was then stirred at 30° C. for 30 min., then at 50° C. for 2 h, and finally at 80° C. for 1 h. After cooling, the reaction mixture was washed with aq. sat. NaCl soln. and aq. sat. NaHCO₃ soln. The aq. phases were extracted with Et₂O, dried (Na₂SO₄), and concentrated. FC (SiO₂, hexane/Et₂O 20:1) of the crude (26 g) gave 1.74 g (13%) of compound 2. The boiling point of the end product is 95° C. at 0.06 torr (0.08 mbar).

¹H-NMR (400 MHz, CDCl₃): δ5.63-5.60 (tq, J=1.5, 3.5, H—C(7)), 4.63 (quintet, J=1.3, $H_t$—CH=), 4.66-4.65 (br. s, $H_c$—CH=), 2.93 (ddd, J=1.6, 6.3, 14.7, $H_\alpha$—C(3)), 2.81-2.78 (br. s, H—C(1)), 2.44-2.30 (m, C(6)H₂), 2.14 (dt, J=1.6, 14.8, $H_\beta$—C(3)), 2.09 (dd, J=3.4, 12.6, $H_{syn}$—C(9)), 1.89 (dt, J=2.7, 12.6, $H_{anti}$—C(9)), 1.88-1.81 (m, H—C(4)), 1.72 (dd, J=0.6, 1.3, MeC=CH₂), 1.67 (td, J=1.5, 2.3, MeC(8)), 1.36-1.24 (sext t, J=1.8, 7.7, 13.5, MeCH—C(4)), 1.03-1.09 (dqd, J=6.2, 7.3, 13.4, MeCH—C(4)), 0.87 (d, J=7.2, MeCH₂).

¹³C-NMR (100 MHz, CDCl₃): δ212.75 (s, CO), 151.13 (s, C(5)C=), 134.71 (s, C(8)), 125.04 (d, C(7)), 109.09 (t, CH₂=), 53.98 (d, C(1)), 47.24 (d, C(4)), 40.07 (s, C(5)), 39.52 (t, C(6)), 36.64 (t, C(3)), 32.19 (t, C(9)), 22.48 (t, CH₂Me), 21.97 (q, MeC(8)), 18.76 (q, MeC=CH₂), 12.77 (q, MeCH₂).

MS (EI): 219 (5), 218 (28), 203 (5), 190 (4), 189 (14), 175 (9), 162 (4), 161 (15), 148 (5), 147 (16), 145 (5), 136 (9), 135 (26), 134 (44), 133 (56), 132 (12), 131 (6), 126 (5), 125 (7), 121 (19), 120 (20), 119 (100), 117 (17), 115 (15), 112 (5), 111 (68), 108 (12), 107 (26), 106 (17), 105 (74), 103 (9), 97 (17), 95 (20), 94 (15), 93 (90), 92 (34), 91 (84), 83 (28), 81 (14), 80 (8), 79 (34), 78 (12), 77 (47), 42 (17), 65 (20), 55 (39), 53 (21), 51 (10), 41 (55), 39 (28), 29 (13), 27 (11).

IR: $\nu_{max}$ 2963, 2928, 2876, 1707, 1678, 1638, 1448, 1379, 1225, 1153, 1089, 1062, 1009, 916, 889, 857, 811, 786, 727 cm⁻¹.

$[\alpha]_D^{22}$=−572.7 (1.07 in EtOH)

Odour description: ambery, woody, spicy

EXAMPLE 3

(1S*3S*4S*5R*)-5-Isopropenyl-3,4,8-trimethylbicyclo[3.3.1]non-7-en-2-one (3)

At 0° C., 15.3 ml of a soln. of LDA (2M in THF/heptane/ethylbenzene, 31 mmol, 2.5 eq.) was treated dropwise with a soln. of 2.5 g of 5-Isopropenyl-4,8-dimethylbicyclo[3.3.1]non-7-en-2-one (12 mmol) in 25 ml THF. The reaction mixture was stirred 1.5 h at 0° C., treated with 2.6 ml methyl iodide (41.7 mmol, 3.4 eq.), stirred at 25° C. for 3 h, and poured into 1M aq. HCl soln. Extraction with MTBE (2×80 ml), washing of the org. phase with H₂O, aq. sat. NaCl soln., drying (MgSO₄) gave 3.6 g crude. FC (hexane/MTBE 24:1) gave 0.56 g (21%) of compound 3. The boiling point of the end product is 120° C. at 0.08 mbar. $R_f$ (hexane/MTBE 24:1) 0.26.

¹H-NMR (400 MHz, CDCl₃): δ5.54-5.50 (m, H—C(7)), 4.78 (quintet, J=1.3, $H_t$—CH=), 4.72-4.70 (br. s, $H_c$—CH=), 2.82-2.78 (br. s, H—C(1)), 2.35-2.22 (m, C(6)H₂, $H_{syn}$—C(9), H—C(3)), 1.84 (dq (quintet), J=7.3, H—C(4)), 1.79 (td, J=1.6, 2.3, MeC(8)), 1.72 (dd, J=0.9, 1.6, MeC=CH₂), 1.70 (dd, J=2.3, 13.0, $H_{anti}$—C(9)), 1.20 (d, J=7.5, Me—C(3)), 0.86 (d, J=7.2, Me—C(4)).

¹H-NMR (400 MHz, C₆D₆): δ5.24-5.20 (m, H—C(7)), 4.78 (quintet, J=1.4, $H_t$—CH=), 4.63-4.60 (br. s, $H_c$—CH=), 2.71-2.67 (br. s, H—C(1)), 2.10-2.03 (m, $H_\beta$—C(6)), 2.07 (dq (quintet), J=7.5, H—C(3)), 1.91 (ddd, J=1.9, 2.8, 13.0, $H_{syn}$—C(9)), 1.93-1.85 (ddt, J=1.8, 4.6, 13.0, $H_\alpha$—C(6)), 1.76 (td, J=1.6, 2.3, MeC(8)), 1.55 (dq (quintet), J=7.3, H—C(4)), 1.54 (dd, J=0.9, 1.6, MeC=CH₂), 1.35 (dd, J=2.9, 13.0, $H_{anti}$—C(9)), 1.12 (d, J=7.3, Me—C(3)), 0.69 (d, J=7.2, Me—C(4)).

¹³C-NMR (100 MHz, CDCl₃): δ212.75 (s, CO), 151.01 (s, C(5)C=), 132.72 (s, C(8)), 124.48 (d, C(7)), 109.60 (t, CH₂=), 51.98 (d, C(1)), 48.25 (br. d, C(3)), 41.15 (br. d, C(4)), 39.35 (t, C(6)), 39.33 (s, C(5)), 29.99 (t, C(9)), 21.58 (q), 20.12 (q), 19.50 (br. q), 18.22 (q).

¹³C-NMR (100 MHz, C₆D₆): δ210.1 (s, CO), 151.0 (s, C(5)C=), 133.3 (s, C(8)), 123.9 (d, C(7)), 110.1 (t, CH₂=), 51.8 (d, C(1)), 47.4 (br. d, C(3)), 40.6 (br. d, C(4)), 39.7 (s, C(5)), 39.4 (t, C(6)), 30.2 (t, C(9)), 21.8 (q, Me—C(8)), 20.6 (q, MeC=CH₂), 17.9 (br. q, Me—C(3)), 17.6 (q, Me—C(4)).

MS (EI): 218 (27), 203 (8), 190 (8), 185 (3), 175 (8), 161 (11), 147 (19), 133 (66), 119 (100), 111 (47), 107 (47), 105 (72), 93 (72), 91 (76), 83 (57), 77 (43), 65 (18), 55 (48), 41 (62).

IR: $\nu_{max}$ 2969, 2934, 1708, 1636, 1448, 1376, 1233, 1155, 1092, 1061, 1040, 994, 955, 919, 890, 814, 781, 734, 649 cm⁻¹.

$[\alpha]_D^{22}$=−655.3 (c=0.99, EtOH)

Odour description: woody, green, floral, rosy, ambery

EXAMPLE 4

5-Isopropenyl-3,3,4,8-tetramethylbicyclo[3.3.1]non-7-en-2-one (4)

At 55° C., a mixture of 9.9 g KOH (176 mmol, 15 eq.) in 40 ml DMSO was treated dropwise with a soln. of 2.4 g of of 5-isopropenyl-4,8-dimethyl-bicyclo[3.3.1]non-7-en-2-one (11.7 mmol) in 3.7 ml methyliodide (59 mmol, 5 eq.). The reaction mixture was stirred 1.5 h at 60° C., treated with 2.0 ml methyl iodide (32 mmol, 2.7 eq.), stirred at 60° C. for 1.5 h, treated with 1.7 ml methyl iodide (27 mmol, 2.3 eq.), stirred at 60° C. for 1.5 h, cooled, and poured into 200 ml of 2M aq. HCl soln. Extraction with hexane (2×100 ml), washing of the org. phase with H₂O, aq. sat. NaCl soln., drying (MgSO₄) gas 2.6 g crude. FC (hexane/MTBE 15:1) gave 0.7 g (26%) of compound 4. The boiling point of the end product is 120° C. at 0.08 mbar. $R_f$ (hexane/MTBE 15:1) 0.27.

¹H-NMR (400 MHz, CDCl₃): δ5.55-5.51 (m, H—C(7)), 4.83 (quintet, J=1.4, $H_t$—CH=), 4.75-4.73 (br. s, $H_c$—CH=), 2.86-2.83 (m, H—C(1)), 2.43-2.35 (m, H—C(6)), 2.33-2.25 (m, H—C(6)), 2.28 (ddd, J=1.6, 3.0, 13.0, $H_{anti}$—C(9)), 1.96 (qd, J=1.0, 7.4, H—C(4)), 1.80 (dd, J=0.5, 1.3, MeC=CH₂), )), 1.70 (dd, J=1.1, 13.0, $H_{syn}$—C(9)), 1.70 (q, J=1.8, MeC(8)), 1.21 (s, Me), 1.07 (s, Me), 0.85 (d, J=7.5, MeC(4)).

¹³C-NMR (100 MHz, CDCl₃): δ214.58 (s, CO), 151.65 (s, C(5)C=), 133.10 (s, C(8)), 124.94 (d, C(7)), 109.91 (t, CH₂=), 52.58 (d, C(1)), 47.15 (s, C(3)), 45.15 (d, C(4)), 40.64 (s, C(5)), 40.49 (t, C(6)), 31.33 (q), 30.55 (t, C(9)), 25.21 (q), 22.18 (q), 21.44 (q), 13.95 (q).

MS (EI): 218 (27), 203 (8), 190 (8), 185 (3), 175 (8), 161 (11), 147 (19), 133 (66), 119 (100), 111 (47), 107 (47), 105 (72), 93 (72), 91 (76), 83 (57), 77 (43), 65 (18), 55 (48), 41 (62).

IR: $\nu_{max}$ 2969, 2934, 1708, 1636, 1448, 1376, 1233, 1155, 1092, 1061, 1040, 994, 955, 919, 890, 814, 781, 734, 649 cm⁻¹.

Odour description: woody, ambery

EXAMPLE 5

(1S*4S*5R*)-5-Isopropenyl-8,8-dimethoxy-2,6-dimethylbicyclo[3.3.1]non-2-ene (5)

A soln. of 1.5 g of 5-isopropenyl-4,8-dimethylbicyclo[3.3.1]non-7-en-2-one (7.3 mmol), 1.4 g para-toluenesulfonic acid mono hydrate (7.4 mmol 1 eq.), and 0.78 g trimethylorthoformate (7.4 mmol, 1 eq.) in 50 ml methanol was heated at 60° C. for 66 h. The reaction mixture was then cooled and poured into aq. sat. NaHCO₃ soln. (20 ml). Extraction with MTBE (2×80 ml) followed by washing of the aq. phases with H₂O and aq. sat. NaCl soln., drying of org. phases (MgSO₄) led to 1.8 g of crude product. FC (SiO₂, Hexane/MTBE 30:1) gave 1.7 g (92%) of compound 5 as colorless liquid. The boiling point of the end product is 130° C. at 0.08 mbar. $R_f$ (hexane/MTBE 8:1) 0.57.

¹H-NMR (400 MHz, CDCl₃): δ5.48 (tq, J=1.4, 3.7, H—C(7)), 4.63 (quintet, J=1.4, $H_t$—CH=), 4.61-4.60 (br. s, $H_c$—CH=), 3.20 (s, OMe), 3.17 (s, OMe), 2.49-2.45 (m, irrad. at 1.43→changes, H—C(1)), 2.17-2.02 (m, C(6)H₂), 1.97 (dd, J=3.0, 12.4, irrad. at 1.43→br. d, J≈4.0, $H_{syn}$—C(9)), 1.88 (dd, J≈6.2, 14.4, $H_α$—C(3)), 1.90-1.81 (m, irrad. at 1.43→changes, H—C(4)), 1.79 (td, J=1.7, 2.1, MeC(8)), 1.66 (dd, J=0.6, 1.4, MeC=CH₂), 1.69-1.61 (m, irrad. at 2.47→changes, $H_β$—C(3)), 1.43 (ddd, J=1.6, 3.5, 12.5, irrad. at 2.47→dd, J=1.4, 12.6, $H_{anti}$—C(9)), 0.88 (d, J=7.7, MeC(4)).

¹H-NMR (400 MHz, C₆D₆): δ5.49-5.45 (m, H—C(7)), 4.77-4.73 (m, CH₂=), 3.05 (s, OMe), 3.03 (s, OMe), 2.49-2.44 (m, H—C(1)), 2.12-2.05 (m, H—C(6)), 2.05 (dd, J=2.8, 12.3, $H_{syn}$—C(9)), 1.96 (td, J=1.7, 2.1, MeC(8)), 1.99-1.91 (m, H—C(6)), 1.93 (dd, J=6.2, 13.5, $H_α$—C(3)), 1.71 (quintet t, J=1.7, 7.2, H—C(4)), 1.63 (dt, J=1.9, 13.5, $H_β$—C(3)), 1.61 (dd, J=0.6, 1.2, MeC=CH₂), 1.48 (ddd, J=1.8, 3.5, 12.4, $H_{anti}$—C(9)), 1.06 (d, J=7.3, MeC(4)).

¹³C-NMR (100 MHz, CDCl₃): δ152.59 (s, C(5)C=), 135.79 (s, C(8)), 124.07 (d, C(7)), 107.32 (t, CH₂=), 102.98 (s, C(2)), 47.59 (q, OMe), 47.47 (q, OMe), 40.59 (d), 40.14 (t, C(6)), 39.12 (s, C(5)), 37.05 (d), 32.53 (t, C(9)), 27.90 (t, C(3)), 24.45 (q), 18.33 (q), 17.41 (q).

¹³C-NMR (100 MHz, C₆D₆): δ152.71 (s, C(5)C=), 136.37 (s, C(8)), 124.13 (d, C(7)), 107.78 (t, CH₂=), 103.25 (s, C(2)), 47.46 (q, OMe), 46.38 (q, OMe), 40.90 (d), 40.61 (t, C(6)), 39.65 (s, C(5)), 37.47 (d), 33.36 (t, C(9)), 27.30 (t, C(3)), 24.97 (q), 18.57 (q), 18.02 (q).

MS (EI): 250 (0.2), 218 (31), 203 (19), 187 (5), 171 (12), 137 (57), 115 (100), 91 (35), 77 (23), 69 (15), 55 (16), 41 (35).

IR: $ν_{max}$ 2945, 2829, 1638, 1451, 1366, 1308, 1194, 1160, 1130, 1110, 1086, 1051, 1018, 972, 953, 922, 886, 846, 799, 772 cm⁻¹.

$[α]_D^{22}$ =−150.1 (c=1.00, EtOH)

Odour description: ambery, woody, fruity, sweet

EXAMPLE 6

(1S*4S*5R*)-4,8-Dimethyl-5-isopropenylspiro[bicyclo[3.3.1]nonane-2,2'-[1,3]dioxolane] (6)

A soln. of 2.0 g of 5-isopropenyl-4,8-dimethylbicyclo[3.3.1]non-7-en-2-one (9.8 mmol) in 100 ml cyclohexane was treated with 1.8 g ethyleneglycol (2.9 mmol, 3.0 eq.) and 0.2 g para-toluenesulfonic acid mono hydrate (1.0 mmol 0.1 eq.). The soln. obtained was heated at reflux for 3 h (Dean-Stark apparatus), cooled and poured into aq. sat. NaHCO₃ soln. (100 ml). Extraction with MTBE (2×80 ml) followed by washing of the aq. phases with H₂O (100 ml) and aq. sat. NaCl soln. (150 ml), drying of org. phases over MgSO₄ led to 2.6 g of crude product. FC (SiO₂, hexane/MTBE 19:1) gave 0.76 g (31%) of compound 6 as colorless liquid. The boiling point of the end product is 130° C. at 0.09 mbar. $R_f$ (hexane/MTBE 19:1) 0.47.

¹H-NMR (400 MHz, CDCl₃): δ5.49 (tq, J=1.4, 3.5, H—C(7)), 4.64 (quintet, J=1.4, $H_t$—CH=), 4.62-4.60 (br. s, $H_c$—CH=), 4.03-3.88 (m, OCH₂CH₂O), 2.21-2.18 (br. s, H—C(1)), 2.17 (dd, J=6.2, 13.8, $H_α$—C(3)), 2.14-2.09 (m, C(6)H₂), 2.09 (dd, J=2.9, 12.9, $H_{syn}$—C(9)), 1.92 (quintet t, J=1.7, 7.2, H—C(4)), 1.79 (td, J=1.5, 2.2, MeC(8)), 1.66 (dd, J=0.6, 1.3, MeC=CH₂), 1.52 (ddd, J=1.9, 3.4, 12.6, $H_{anti}$—C(9)), 1.36 (dt, J=1.8, 13.9, $H_β$—C(3)), 0.89 (d, J=7.2, MeC(4)).

¹³C-NMR (100 MHz, CDCl₃): δ152.43 (s, C(5)C=), 135.84 (s, C(8)), 123.96 (d, C(7)), 111.52 (s, C(2)), 107.53 (t, CH₂=), 64.27 (t, OCH₂), 63.46 (t, OCH₂), 43.56 (d), 39.89 (t, C(6)), 38.92 (s, C(5)), 37.34 (d), 34.16 (t, C(9)), 28.70 (t, C(3)), 23.97 (q), 18.32 (q), 16.88 (q).

MS (EI): 248 (1), 233 (0.2), 203 (0.3), 147 (2), 133 (3), 119 (5), 113 (100), 105 (6), 91 (9), 86 (4), 77 (5), 69 (9), 41 (9).

IR: $ν_{max}$ 2962, 2885, 1638, 1450, 1368, 1308, 1162, 1129, 1110, 1083, 1063, 1042, 1020, 975, 953, 925, 887, 845, 831, 801 cm⁻¹.

$[α]_D^{22}$=−142.8 (c=0.51, EtOH)

Odour description: fruity, spicy, woody

EXAMPLE 7

5-Isopropenyl-4,8-dimethylbicyclo[3.3.1]non-7-en-2-ol (7A and 7B)

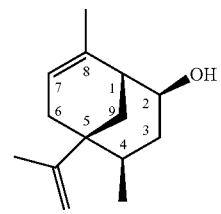

7A

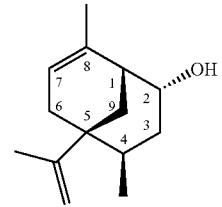

7B

At 5° C., a soln. of 1 g of 5-isopropenyl-4,8-dimethylbicyclo[3.3.1]non-7-en-2-one (4.9 mmol) in 5 ml ethanol was treated with 0.37 g NaBH₄ (9.8 mmol, 2 eq.). The reaction mixture was then stirred 2 h at 25° C., poured into 1N aq. HCl soln., and extracted with Et₂O. The org. phase was washed with aq. sat. NaCl soln., dried, and concentrated. FC (hexane/Et₂O 9:1 to 9:2) of the crude (1 g, 7A/7B 30:70) gave 0.1 g 7A (10%), 0.2 g 7A/7B (1:1, 20%), and 0.4 g 7B (40%).

(1S*2R*4S*5R*)-5-Isopropenyl-4,8-dimethylbicyclo[3.3.1]non-7-en-2-ol (7A (exo))

Boiling point: 100° C. at 0.06 torr (0.08 mbar).

¹H-NMR (400 MHz, CDCl₃): δ5.44 (tq, J=1.4, 3.5, H—C(7)), 4.67-4.64 (m, C=CH₂), 3.90 (dt, J=2.8, 2.9, H—C(2)), 2.29-2.25 (m, H—C(1)), 2.20 (dd, J=3.0, 12.6, $H_{syn}$—C(9)), 2.10-2.05 (m, C(6)H₂), 2.02 (ddd, J=3.7, 6.2, 14.9, $H_α$—C(3)), 1.82-1.75 (m, H—C(4)), 1.69 (td, J=1.6, 2.1, MeC(8)), 1.66 (dd, J=0.6, 1.1, MeC=CH₂), 1.45 (ddt, J=1.6, 1.8, 14.8, $H_β$—C(3)), 1.37 (ddd, J=1.2, 1.7, 12.6, $H_{anti}$—C(9)), 0.98 (d, J=7.3, MeC(4)).

¹³C-NMR (100 MHz, CDCl₃): δ152.93 (s, C(5)C=), 135.27 (s, C(8)), 123.66 (d, C(7)), 107.21 (t, CH₂=), 68.41

(d, C(2)), 43.39 (d), 39.36 (t, C(6)), 39.18 (s, C(5)), 35.96 (d), 32.99 (t, C(9)), 24.12 (t, C(3)), 22.26 (q, MeC(8)), 18.87 (q, MeC=CH$_2$), 17.91 (q, MeC(4)).

MS (EI): 206 (17), 188 (44), 173 (32), 159 (14), 147 (19), 145 (26), 133 (58), 119 (66), 107 (71), 105 (77), 93 (100), 77 (50), 71 (24), 55 (36), 41 (70).

$[\alpha]_D^{22}$=−141.4 (c=0.89, EtOH)

Odour description: floral, agrestic, rosy, green

(1S*2S*4S*5R*)-5-Isopropenyl-4,8-dimethylbicyclo[3.3.1]non-7-en-2-ol (7B(endo))

Boiling point: 80° C. at 0.05 torr (0.07 mbar).

$^1$H-NMR (400 MHz, CDCl$_3$): δ5.60 (tq, J=1.5, 3.5, H—C(7)), 4.63 (quintet, J=1.4, H$_t$—CH=), 4.58-4.56 (br. s, H$_c$—CH=), 4.03 (dt, J=4.4, 11.5, irrad. at 2.48→dd, J≈4.4, 11.2, H—C(2)), 2.50-2.45 (m, irrad. at 4.03→changes, H—C(1)), 2.12-2.00 (br. s, C(6)H$_2$), 1.89 (br. quintet t, J=1.7, 7.1, H—C(4)), 1.86-1.76 (m, irrad. at 4.03→changes, irrad. at 2.48→changes, H$_{syn}$—C(9)), H$_\alpha$—C(3)), 1.81 (td, J=1.6, 2.2, MeC(8)), 1.64 (br. d, J=0.8, MeC=CH$_2$), 1.57 (ddd, J=1.8, 3.7, 12.8, irrad. at 2.48→dd, J≈2.0, 12.8, H$_{anti}$—C(9)), 1.55 (dddd, J=1.4, 1.8, 4.4, 12.4, irrad. at 4.03→dt, J≈1.9, 11.6, irrad. at 2.48→dd, J=2.0, 4.4, 12.4, H$_\beta$—C(3)), 1.33-1.21 (br. s, OH), 0.80 (d, J=7.2, MeC(4)).

$^1$H-NMR (400 MHz, C$_6$D$_6$): δ5.52 (tq, J=1.5, 3.4, H—C(7)), 4.68 (quintet, J=1.4, H$_t$—CH=), 4.63-4.61 (br. s, H$_c$—CH=), 3.73 (dt, J=4.4, 11.6, H—C(2)), 2.29-2.25 (m, H—C(1)), 2.03-1.95 (m, H—C(6)), 1.91 (td, J=1.6, 2.1, MeC(8)), 1.88-1.80 (m, H—C(6)), 1.77 (td, J=5.3, 12.2, H$_\alpha$—C(3)), 1.61 (br. quintet t, J=1.8, 7.2, H—C(4)), 1.62-1.57 (m, H$_{syn}$—C(9)), 1.52 (dd, J=0.6, 1.3, MeC=CH$_2$), 1.49 (ddd, J=1.8, 3.7, 12.7 H$_{anti}$—C(9)), 1.30 (dddd, J=1.3, 2.0, 4.4, 12.6, H$_\beta$—C(3)), 0.71 (d, J=7.2, MeC(4)), 0.66-0.57 (br. s, OH).

$^{13}$C-NMR (100 MHz, CDCl$_3$): δ152.26 (s, C(5)C=), 133.63 (s, C(8)), 124.24 d, C(7)), 107.48 (t, CH$_2$=), 69.53 (d, C(2)), 42.84 (d), 39.94 (t, C(6)), 38.64 (s, C(5)), 37.23 (d), 34.61 (t, C(9)), 29.57 (t, C(3)), 25.05 (q, MeC(8)), 18.26 (q, MeC=CH$_2$), 16.15 (q, MeC(4)).

MS (EI): 206 (17), 188 (44), 173 (32), 159 (14), 147 (19), 145 (26), 133 (58), 119 (66), 107 (71), 105 (77), 93 (100), 77 (50), 71 (24), 55 (36), 41 (70).

IR: ν$_{max}$ 3282, 2966, 2933, 2880, 1637, 1443, 1375, 1355, 1329, 1296, 1250, 1162, 1079, 1047, 1029, 998, 887, 821, 792, 632 cm$^{-1}$.

$[\alpha]_D^{22}$=−226.0 (c=0.98, EtOH)

Odour description: floral, isononanol-like, grapefruit

EXAMPLE 8

5-Isopropenyl-2,4,8-trimethylbicyclo[3.3.1]non-7-en-2-ol (8A and 8B)

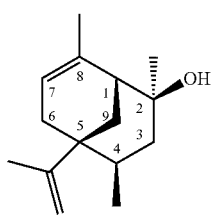

8A

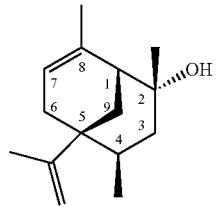

8B

At 5° C., a soln. of 1 g of 5-isopropenyl-4,8-dimethylbicyclo[3.3.1]non-7-en-2-one (4.9 mmol) in 15 ml THF was treated dropwise with 21 ml 1.4M MeLi in Et$_2$O (29.4 mmol, 6 eq.). The reaction mixture was stirred 5 h at 5° C., warmed to 25° C. overnight, poured into aq. sat. NH$_4$Cl soln., and extracted with Et$_2$O. The org. phase was washed with aq. sat. NaCl soln., dried, and concentrated. FC (SiO$_2$, hexane/Et$_2$O 9:1) of the crude (1.2 g, starting material/OH exo/OH endo 17:65:18)gave 0.2 g of starting material (20%), 0.5 g 8A (46%), 0.25 g 8A/8B (1:1, 23%), and 0.1 g 8B (9%).

(1S*2R*4S*5R*)-5-Isopropenyl-2,4,8-trimethylbicyclo[3.3.1]non-7-en-2-ol (8A(exo))

Boiling point: 80° C. at 0.07 torr (0.09 mbar)

$^1$H-NMR (400 MHz, CDCl$_3$): δ5.44 (tq, J=1.5, 3.7, H—C(7)), 4.66-4.64 (br. s, H$_c$—CH=), 4.63 (quintet, J=1.4, H$_t$—CH=), 2.26 (dd, J=3.1, 12.5, H$_{syn}$—C(9)), 2.10-2.05 (m, C(6)H$_2$, H—C(1)), 1.92 (dd, J=6.1, 14.4, H$_\alpha$—C(3)), 1.81 (quintet t, J=1.5, 7.2, H—C(4)), 1.77 (td, J=1.5, 2.2, MeC(8)), 1.67 (dd, J=0.6, 1.3, MeC=CH$_2$), 1.38 (ddd, J=1.5, 3.0, 12.5, H$_{anti}$—C(9)), 1.31 (dt, J=1.6, 14.4, H$_\beta$—C(3)), 1.27-1.21 (br. s, OH), 1.18 (s, MeC(2)), 0.98 (d, J=7.3, MeC(4)).

$^{13}$C-NMR (100 MHz, CDCl$_3$): δ152.70 (s, C(5)C=), 135.83 (s, C(8)), 124.48 (d, C(7)), 107.11 (t, CH$_2$=), 73.24 (s, C(2)), 47.84 (d, C(1)), 39.91 (t, C(6)), 38.86 (s, C(5)), 38.49 (t), 36.85 (d, C(4)), 31.31 (q, MeC(2)), 26.92 (t), 24.57 (q, MeC(8)), 18.06, 18.03 (2q, MeC=CH$_2$, MeC(4)).

MS (EI): 220 (6), 202 (22), 187 (18), 162 (48), 147 (21), 135 (56), 119 (55), 107 (66), 93 (74), 85 (100), 77 (39), 67 (26), 55 (28), 43 (81).

IR: ν$_{max}$ 3417, 2968, 2928, 2833, 1640, 1446, 1372, 1329, 1302, 1210, 1151, 1121, 1104, 1033, 942, 926, 886, 832, 800, 781 cm$^{-1}$.

Odour description: fruity, agrestic, rosy, earthy

(1S*2S*4S*5R*)-5-Isopropenyl-2,4,8-trimethylbicyclo[3.3.1]non-7-en-2-ol (8B(endo))

Boiling point: 60° C. at 0.06 torr (0.08 mbar).

$^1$H-NMR (400 MHz, CDCl$_3$): δ5.56 (tq, J=1.6, 3.5, H—C(7)), 4.62 (quintet, J=1.4, H$_t$—CH=), 4.60-4.58 (br. s, H$_c$—CH=), 2.18-2.14 (m, H—C(1)), 2.13-2.08 (m, C(6)H$_2$), 1.97 dd, J=6.3, 13.1, H$_\alpha$—C(3)), 1.90 (quintet t, J=1.5, 7.2, H—C(4)), 1.86 (dd, J=3.0, 13.1, H$_{syn}$—C(9)), 1.84 (td, J=1.5, 2.2, MeC(8)), 1.54 (ddd, J=1.8, 3.5, 13.1, H$_{anti}$—C(9)), 1.42 (dt, J=1.4, 13.0, H$_\beta$—C(3)), 1.41-1.39 (br. s, MeC=CH$_2$), 1.32-1.22 (br. s, OH), 1.26 (s, MeC(2)), 0.83 (d, J=7.5, MeC(4)).

$^{13}$C-NMR (100 MHz, CDCl$_3$): δ152.13 (s, C(5)C=), 135.70 (s, C(8)), 124.14 (d, C(7)), 107.24 (t, CH$_2$=), 73.32 (s, C(2)), 47.42 (d, C(1)), 40.90, 40.27 (2t, C(3), C(6)), 38.71 (s, C(5)), 37.23 (d, C(4)), 29.24 (t), 29.02 (q, MeC(2)), 25.46 (q, MeC(8)), 18.18, 17.49 (2q, MeC=CH$_2$, MeC(4).

MS (EI): 220 (4), 202 (24), 187 (16), 162 (46), 147 (22), 135 (56), 119 (55), 107 (66), 93 (74), 85 (100), 77 (39), 67 (26), 55 (28), 43 (81).

IR: $v_{max}$ 3452, 2924, 2881, 1638, 1448, 1376, 1289, 1258, 1160, 1140, 1109, 1061, 1019, 943, 931, 907, 887, 829, 800, 656 cm$^{-1}$.

Odour description: fruity, rosy

EXAMPLE 9

5-Isopropyl-4,8-dimethylbicyclo[3.3.1]nonan-2-one (9)

At 25° C., a mixture of 1 g 5-isopropenyl-4,8-dimethylbicyclo[3.3.1]non-7-en-2-one (4.9 mmol) and 50 mg 10% Pd/C in 10 ml MeOH was stirred under 10 bar of H$_2$ for 5 h. Filtration (Celite®), concentration, and FC (SiO$_2$, hexane/Et$_2$O 100:7) gave 0.22 g (22%) of compound 9. The boiling point of the end product is 75° C. at 0.07 torr (0.09 mbar).

$^1$H-NMR (400 MHz, CDCl$_3$): δ2.69 (dd, J=8.2, 17.4, H$_\alpha$—C(3)), 2.38-2.31 (br. s, H—C(1)), 2.20 (br. d, J=17.1, H$_\beta$—C(3)), 2.23-2.12 (m, 1H), 1.79-1.38 (m, 8H), 0.93 (d, J=7.1, Me), 0.88 (d, J=6.8, Me), 0.84 (d, J=6.2, Me), 0.82 (d, J=6.5, Me).

$^1$H-NMR (400 MHz, C$_6$D$_6$): δ2.39 (dd, J=8.1, 17.2, H$_\alpha$—C(3)), 2.31-2.26 (m, H—C(1)), 2.12 (br. d, J=17.3, H$_\beta$—C(3)), 1.73 (br. quintet, J=7.1, H—C(4)), 1.53-1.41 (m, H$_{anti}$—C(9), H—C(7)), 1.40-1.30 (m, H—C(6), H—C(8), CHMe$_2$), 1.29 (dt, J=2.3, 13.5, H$_{anti}$—C(9)), 1.23-1.10 (m, H—C(7), H—C(6)), 0.62 (d, J=6.7, MeC(8)), 0.69 (d, J=6.8, MeCHMe), 0.68 (d, J=7.2, MeC(4)), 0.62 (d, J=6.9, MeCHMe).

$^{13}$C-NMR (100 MHz, CDCl$_3$): δ214.61 (s, CO), 52.70 (d), 49.67 (t), 37.65 (d), 35.51 (s), 34.33 (d), 33.36 (t), 32.98 (d), 29.93 (t), 28.19 (t), 19.86 (q), 18.34 (q), 17.11 (q), 15.84 (q).

$^{13}$C-NMR (100 MHz, C$_6$D$_6$): δ210.00 (s, CO), 52.88 (d, C(1)), 49.86 (t, C(3)), 37.68 (d, C(4)), 35.72 (s, C(5)), 34.50 (d, C(8)), 33.51 (t, C(9)), 33.17 (d, CHMe$_2$), 30.25 (t, C(7)), 28.44 (t, C(6)), 20.23 (q, Me—C(8)), 18.38 (q, Me—C(4)), 17.28, 16.03 (2q, Me$_2$C).

MS (EI): 208 (22), 193 (7), 190 (3), 165 (36), 147 (14), 137 (58), 123 (24), 109 (15), 95 (84), 81 (100), 67 (30), 55 (36), 41 (45).

$[\alpha]_D^{22}$=−108.8 (c=1.06, EtOH).

Odour description: fruity, agrestic, rosy, woody

EXAMPLE 10

(1S*5R*)-5-Isopropenyl-8-methylbicyclo[3.3.1]non-7-en-2-one (10)

A mixture of 20.0 g acryloyl chloride (0.22 mol) and 3.01 g zinc chloride (0.02 ml, 0.1 eq.) in 150 ml ethylene chloride was treated with a soln. of 350 ml α-pinene ((1S-(−)/(1R)-(+) 90:10, 2.20 mol, 10 eq.) in 250 ml ethylene chloride and the resulting mixture was stirred 1 h at 25° C. and 4 h at 50° C. After cooling, the reaction mixture was washed with aq. sat. NaCl soln. and aq. sat. NaHCO$_3$ soln. The aq. phases were extracted with Et$_2$O, dried (Na$_2$SO$_4$), and concentrated. The crude product (48 g) was filtered (SiO$_2$, hexane/Et$_2$O 200:6→200:10) and the residue (1.42 g) treated with 300 mg LiOH.H$_2$O in 15 ml MeOH at 25° C. for 7 h. The resulting mixture was poured into aq. sat. NaCl soln., extracted with hexane and the org. phases dried with Na$_2$SO$_4$, FC (SiO$_2$, hexane/Et$_2$O 30:1) gave 347 mg (0.8%) of compound 10. Boiling point: 80° C. at 0.07 torr (0.09 mbar).

$^1$H-NMR (400 MHz, CDCl$_3$): δ5.65 (tq, J=1.5, 3.3, H—C(7)), 4.5-4.743 (br. s, H$_c$—CH=), 4.72 (quintet, J=1.4, H$_t$—CH=), 2.85 (br. t, J=3.1, H—C(1)), 2.79 (ddd, J=6.8, 13.7, 15.4, H$_\alpha$—C(3)), 2.375 (br. d, J=18.8, H—C(6)), 2.295 (dddd, J=1.9, 3.9, 5.8, 18.9, H—C(6)), 2.12 (dddd, J=1.3, 2.2, 5.9, 15.3, H$_\beta$—C(3)), 2.13-2.06 (m, H$_\alpha$—C(4)), 2.03-2.00 (br. s, C(9)H$_2$), 1.78 (dd, J=0.7, 1.3, MeC=CH$_2$), 1.73 (dddd, J=1.5, 6.0, 13.4, H—C$_\beta$(4)), 1.67 (dt, J=1.6, 2.2, MeC(8)).

$^{13}$C-NMR (100 MHz, CDCl$_3$): δ212.05 (s, CO), 152.28 (s, C(5)C=), 133.76 (s, C(8)), 125.20 (d, C(7)), 108.06 (t, CH$_2$=), 53.65 (d, C(1)), 38.13 (t), 36.68 (t), 36.00 (s, C(5)), 35.64 (t), 34.25 (t), 21.99 (q, MeC(8)), 19.06 (q, MeC=CH$_2$).

MS (EI): 190 (16), 175 (5), 162 (1), 157 (4), 147 (9), 133 (27), 119 (28), 105 (58), 98 (21), 93 (100), 91 (65), 83 (95), 77 (37), 65 (17), 55 (20), 41 (42).

IR: $v_{max}$ 2929, 1737, 1712, 1637, 1443, 1379, 1241, 1151, 1119, 1058, 993, 890, 789 cm$^{-1}$.

$[\alpha]_D^{22}$=−55.0 (c=0.79, EtOH)

Odour description: woody (pine, cedarwood), ambery, sweet

EXAMPLE 11

(1S*3R*4S*5R*)-5-Isopropenyl-3,4,8-trimethylbicyclo[3.3.1]non-7-en-2-one (11)

Method a) A mixture of 11.81 g 2-methyl-but-2-enoyl chloride (0.10 mol) and 1.36 g zinc chloride (0.01 mol, 0.1 eq.) in 100 ml ethylene chloride was treated with a soln. of 136 g α-pinene ((1S)-(−)/(1R)-(+) 90:10, 1 mol, 10 eq.) in 150 ml ethylene chloride and the resulting mixture was stirred 45 min. at 25° C., 2.5 h at 50° C., and 1 h at 80°. After cooling, the reaction mixture was washed with aq. sat. NaCl soln. and aq. sat. NaHCO$_3$ soln. The aq. phases were extracted with Et$_2$O, dried (Na$_2$SO$_4$), and concentrated. The crude product (48 g) filtered (SiO$_2$, hexane/Et$_2$O 200:6→200:13) and the residue (5.1 g) treated with 1 g LiOH.H$_2$O in 75 ml MeOH at 25° C. for 48 h. The resulting mixture was poured into aq. sat. NaCl soln. and extracted with hexane. The combined org. phases were dried (Na$_2$SO$_4$), concentrated and purified by FC (SiO$_2$, hexane/Et$_2$O 100:3) gave 1.6 g (7.1%) of compound 11.

Method b) 15 ml of a soln. of 0.116 M of EtONa in EtOH were treated with 1.5 g of 5-isopropenyl-3,4,8-trimethylbicyclo[3.3.1]non-7-en-2-one and heated 4 h at reflux. The resulting mixture was poured into 50 ml 2M aq. HCl and extracted with 2×50 ml MTBE. The org. phases were washed with 50 ml H$_2$O, 50 ml aq. sat. NaCl soln., and dried. FC (SiO$_2$, hexane/MTBE 20:1) gave 0.75 g (50%) of compound 11. Boiling point: 80° C. at 0.08 mbar.

$^1$H-NMR (400 MHz, CDCl$_3$): δ5.61 (tq, J=1.5, 3.2, H—C(7)), 4.73 (quintet, J=1.3, H$_t$—CH=), 4.64-4.62 (br. s, H$_c$—CH=), 3.26 (qd, J=5.8, 6.7, H—C(3)), 2.83 (br. t, J=3.1, H—C(1)), 2.45-2.33 (m, C(6)H$_2$), 2.13 (qqq, J=2.5, 5.6, 7.0, H—C(4)), 2.11 (dd, J=3.4, 12.6, H$_{syn}$—C(9)), 1.85 (dt, J=2.7, 12.6, H$_{anti}$—C(9)), 1.72 (dd, J=0.8, 1.2, MeC=CH$_2$), 1.66 (dt, J=1.6, 2.3, MeC(8)), 0.93 (d, J=6.7, MeC(3)), 0.63 (d, J=7.1, MeC(4)).

$^{13}$C-NMR (100 MHz, CDCl$_3$): δ214.66 (s, CO), 151.19 (s, C(5)C=), 135.89 (s, C(8)), 124.96 (d, C(7)), 108.94 (t, CH$_2$=), 54.02 (d, C(1)), 46.01 (t, C(3)), 40.96 (s, C(5)), 39.47 (t, C(6)), 39.30 (d, C(4)), 32.16 (t, C(9)), 22.21 (q, MeC(8)), 18.63 (q, MeC=CH$_2$), 12.38, 10.51 (2q, MeC(3), MeC(4)).

MS (EI): 218 (27), 203 (7), 190 (8), 175 (9), 161 (12), 147 (17), 133 (59), 119 (100), 105 (75), 95 (13), 93 (67), 91 (85), 77 (52), 69 (7), 55 (65), 41 (65).

IR: $\nu_{max}$ 2968, 2927, 1708, 1677, 1638, 1446, 1381, 1351, 1238, 1210, 1152, 1103, 1083, 1059, 1003, 869, 830, 802, 790, 659 cm$^{-1}$.

$[\alpha]_D^{22}$=−768.6 (c=0.97, EtOH)

Odour description: fruity, peppery, woody, elemi, gurjun, ambery

EXAMPLE 12

4,8-Dimethyl-5-isopropenyl-8-methoxy-bicyclo[3.3.1]non-7-ene (12A and 12B)

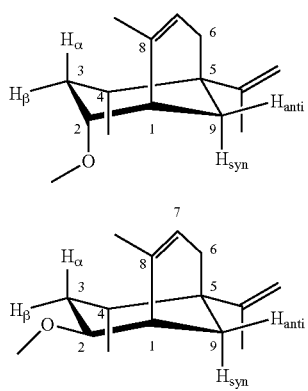

12A

12B

A soln. of 2.9 g of 5-isopropenyl-4,8-dimethylbicyclo[3.3.1]non-7-en-2-ol (14.1 mmol, α/β 58:42) in 30 ml DMF was added dropwise to a suspension of 0.84 g 55-65% sodium hydride (21 mmol, 1.5 eq.) in 30 ml DMF and the resulting mixture was stirred 1.5 h at 25° C., treated with 2.6 ml methyl iodide (41.8 mmol, 3 eq.), heated 4.5 h at 80° C., poured into 50 ml HCl 2M, and extracted with 2×80 ml hexane. The org. phases were washed with 2×100 ml 1:1 aq. sat. NaCl soln./H$_2$O, dried, and concentrated. FC (hexane/MTBE 15:1) of the crude (2.17 g) gave 0.25 g 12A (8.1%), 0.85 g 12B/12A (55:45, 27.4%), and 1.07 g 12B (34.5%).

(1S*2R*4S*5R*)-4,8-Dimethyl-5-isopropenyl-8-methoxy-bicyclo[3.3.1]non-7-ene (12A)

Boiling point: 80° C. at 0.08 mbar.

$^1$H-NMR (400 MHz, CDCl$_3$): δ5.46 (tq, J=1.4, 3.2, H—C(7)), 4.64-4.62 (m, C=CH$_2$), 3.33 (s, MeO), 3.29 (dt, J=2.8, 2.9, H—C(2)), 2.41-2.37 (br. s, H—C(1)), 2.11 (dd, J=3.0, 12.5, H$_{syn}$—C(9)), 2.08-2.05 (m, C(6)H$_2$), 1.81 (ddd, J=3.6, 5.8, 14.6, H$_\alpha$—C(3)), 1.74 (br. quintet, J=7.0, H—C(4)), 1.69 (td, J=1.6, 2.1, MeC(8)), 1.65 (br. t, J=0.9, MeC=CH$_2$), 1.63 (ddt, J=1.5, 1.8, 15.0, ,H$_\beta$—C(3)), 1.33 (br. d, J=12.5, H$_{anti}$—C(9)), 0.91 (d, J=7.2, MeC(4)).

$^{13}$C-NMR (100 MHz, CDCl$_3$): δ153.16 (s, C(5)C=), 135.24 (s, C(8)), 124.13 (d, C(7)), 107.26 (t, CH$_2$=), 77.51 (d, C(2)), 56.11 (q, MeO), 40.59 (d), 39.54 (t, C(6)), 39.26 (s, C(5)), 36.46 (d), 28.29 (t, C(9)), 24.85 (t, C(3)), 22.34 (q, MeC(8)), 18.06 (q, MeC=CH$_2$), 17.92 (q, MeC(4)).

MS (EI): 220 (4), 205 (1), 188 (18), 173 (10), 159 (3), 145 (8), 133 (34), 119 (17), 107 (17), 105 (32), 93 (24), 91 (32), 85 (100), 77 (20), 71 (6), 55 (19), 41 (26).

IR: $\nu_{max}$ 2962, 2925, 2889, 2826, 1638, 1447, 1375, 1193, 1160, 1118, 1108, 1097, 1081, 970, 959, 924, 886, 829, 804, 786 cm$^{-1}$.

$[\alpha]_D^{22}$=−90.8 (c=0.14, EtOH)

Odour description: woody, ambery

(1S*2S*4S*5R*)-4,8-Dimethyl-5-isopropenyl-8-methoxy-bicyclo[3.3.1]non-7-ene (12B)

Boiling point: 80° C. at 0.08 mbar.

$^1$H-NMR (400 MHz, CDCl$_3$): δ5.55 (tq, J=1.6, 3.2, H—C(7)), 4.62 (quintet, J=1.4 H$_r$—CH=), 4.57-4.56 (br. s, H$_{C'}$—CH=), 3.49 (dt, J=4.2, 11.6, H—C(2)), 3.36 (s, MeO), 2.66-2.62 (br. s, H—C(1)), 2.10-2.00 (m, C(6)H$_2$), 1.95-1.85 (br. quintet, J=7.1, H—C(4)), 1.81 (td, J=5.4, 12.2, H$_\alpha$—C(3)), 1.76 (dt, J=1.6, 2.2, MeC(8)), 1.74 (dd, J≈2.8, 13.0, H$_{syn}$—C(9)), 1.64 (dd, J=0.5, 1.3, MeC=CH$_2$), 1.59 (ddd, J=1.8, 3.9, 12.8, H$_{anti}$—C(9)), 1.56 (dddd, J=1.4, 2.0, 4.2, 12.6, H$_\beta$—C(3)), 0.79 (d, J=7.2, MeC(4)).

$^{13}$C-NMR (100 MHz, CDCl$_3$): δ152.58 (s, C(5)C=), 134.29 (s, C(8)), 123.66 (d, C(7)), 107.46 (t, CH$_2$=), 78.58 (d, C(2)), 55.98 (q, MeO), 40.00 (t, C(6)), 39.06 (s, C(5)), 38.53 (d), 37.11 (d), 31.72, 29.58 (2 t, C(9), C(3)), 24.42 (q, MeC(8)), 18.35 (q, MeC=CH$_2$), 16.43 (q, MeC(4)).

MS (EI): 220 (5), 205 (1), 188 (19), 173 (10), 159 (3), 145 (8), 133 (31), 119 (16), 107 (15), 105 (29), 93 (22), 91 (30), 85 (100), 77 (18), 71 (5), 55 (18), 41 (23).

IR: $\nu_{max}$ 2965, 2935, 2890, 2828, 1638, 1451, 1374, 1194, 1176, 1103, 1040, 1011, 975, 945, 923, 887, 820, 793, 625 cm$^{-1}$.

$[\alpha]_D^{22}$=−195.4 (c=0.76, EtOH)

Odour description: woody, ambery, fatty, green

EXAMPLE 13

A Fragrance Composition of Shower Gel

| compound/ingredient | parts by weight 1/1000 |
|---|---|
| Armoise oil | 5 |
| Grisalva (5,5,9-Trimethyl-1-ethyltricyclo[8.4.0.0-4,9]-14-oxatetradecane) | 5 |
| Clary sage oil | 10 |
| Jasmonyl (1,3-Nonanediol acetate) | 10 |
| Limette oil | 10 |
| Patchouli oil | 10 |
| Piconia (Isolongifolanone) | 10 |
| Verbena oil Africa | 10 |
| Oakmoss absolute Tyrol at 50% in DPG | 20 |
| Geranium oil | 25 |
| Rosemary oil | 25 |
| Sandela (3-Isocamphylcyclohexanol) | 25 |
| Lavandin Grosso oil | 30 |
| Cinnamon leaves oil | 30 |
| Juniper oil | 30 |
| Methyl cedryl ketone | 30 |
| Dimyrcetol | 40 |
| Fixolide (7-Acetyl-1,1,3,4,4,6-hexamethyltetralin) | 40 |
| Lilial (p-tert.Butyl-alpha-methyldihydrocinnamic aldehyde) | 40 |
| Neroli essential oil | 45 |
| Bornyl acetate | 50 |
| Cedryl acetate | 50 |
| Para-tert-butylcyclohexyl acetate | 50 |
| Hydroxy citronellal | 50 |
| Irisantheme (alpha-Isomethylionone) | 50 |
| Linalyl acetate | 65 |
| Galaxolide 50% Benzyl benzoate | 65 |
| Lemon oil Italy | 70 |
| Bergamot oil | 90 |
| 5-Isopropenyl-4,8-dimethylbicyclo[3.3.1]non-7-en-2-one (1) | 10 |
| | 1000 |

Adding 5-Isopropenyl-4,8-dimethylbicyclo[3.3.1]non-7-en-2-one (1) to the fragrance composition adds a sophisticated woody-ambery note with fruity (raspberry) undertones. It also imparts more volume to the woody accord in a fir balsam direction.

The invention claimed is:

1. A compound of formula (I)

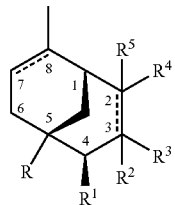

wherein
R is isopropyl or iso-propenyl;
$R^1$ is hydrogen, methyl or ethyl;
$R^2$ and $R^3$ are independently hydrogen, methyl, or ethyl; or
$R^2$ and $R^3$ taken together is ethylidene; or
$R^2$ and $R^3$ taken together is a divalent radical $(CH_2)_2$ which forms cyclopropane together with the carbon atom to which they are attached;
$R^4$ and $R^5$ are independently hydrogen, hydroxy, $C_1$ to $C_3$ alkoxy, or $C_2$ to $C_3$ acyloxy; or
$R^4$ and $R^5$ together with the carbon atom to which they are attached form a 1,3-dioxolane ring or a 1,3-dioxane ring; or
$R^4$ and $R^5$ together with the carbon atom to which they are attached form a carbonyl group;
the bond between C2 and C3 is a single bond, or the dotted line together with the bond between C2 and C3 represents a double bond; and
the bond between C7 and C8 is a single bond, or the dotted line together with the bond between C7 and C8 represents a double bond.

2. A flavour or fragrance composition comprising a compound of formula (I) as defined in claim 1.

3. A flavour or fragrance ingredient comprising a compound of formula (I) as defined in claim 1.

4. A method of manufacturing a flavour or fragrance composition, comprising the step of incorporating a compound of formula (I) as defined in claim 1 to a base material.

5. A method of manufacturing a fragranced application, comprising the incorporation of a compound of formula (I) as defined in claim 1.

6. A method according to claim 5 wherein the fragranced application is selected from the group consisting of perfume, household product, laundry product, body care product and cosmetics.

7. A compound according to claim 1 selected from the group consisting of:
5-isopropenyl-4,8-dimethylbicyclo[3.3.1]non-7-en-2-one;
4-ethyl-5-isopropenyl-8-methylbicyclo[3.3.1]non-7-en-2-one;
5-isopropenyl-3,4,8-trimethylbicyclo[3.3.1]non-7-en-2-one;
5-isopropenyl-3,3,4,8-tetramethylbicyclo[3.3.1]non-7-en-2-one;
5-isopropenyl-8,8-dimethoxy-2,6-dimethylbicyclo[3.3.1]non-2-ene;
4,8-dimethyl-5-isopropenylspiro[bicyclo[3.3.1]nonane-2,2'-[1,3]dioxolane];
5-isopropenyl-4,8-dimethylbicyclo[3.3.1]non-7-en-2-ol;
5-isopropenyl-2,4,8-trimethylbicyclo[3.3.1]non-7-en-2-ol;
5-isopropyl-4,8-dimethylbicyclo[3.3.1]nonan-2-one,
5-isopropenyl-8-methylbicyclo[3.3.1]non-7-en-2-one,
5-isopropenyl-3,4,8-trimethylbicyclo[3.3.1]non-7-en-2-one, and
4,8-dimethyl-5-isopropenyl-8-methoxy-bicyclo[3.3.1]non-7-ene.

8. A flavour or fragrance ingredient comprising a compound of formula (I) as defined in claim 7.

9. A method of manufacturing a flavour or fragrance composition, comprising the step of incorporating a compound of formula (I) as defined in claim 7 to a base material.

10. A method of manufacturing a fragranced application, comprising the incorporation of a compound of formula (I) as defined in claim 7.

11. A method according to claim 10 wherein the fragranced application is selected from the group consisting of perfume, household product, laundry product, body care product and cosmetics.

* * * * *